United States Patent
Suzuki et al.

(10) Patent No.: US 6,617,476 B2
(45) Date of Patent: Sep. 9, 2003

(54) PROCESS FOR PRODUCING AROMATIC RING ALKYLATED PHENOLS

(75) Inventors: Tomoyuki Suzuki, Tsukuba (JP); Fumisato Goto, Tsukuba (JP); Kozo Tanaka, Tsuchiura (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/734,744

(22) Filed: Dec. 13, 2000

(65) Prior Publication Data

US 2001/0004674 A1 Jun. 21, 2001

(30) Foreign Application Priority Data

| Dec. 15, 1999 | (JP) | ............................................ 11-355761 |
| Apr. 20, 2000 | (JP) | ...................................... 2000-119400 |
| Apr. 20, 2000 | (JP) | ...................................... 2000-119401 |
| Jul. 19, 2000 | (JP) | ...................................... 2000-218857 |

(51) Int. Cl.⁷ .......................... C07C 33/34; C07C 37/00
(52) U.S. Cl. ........................ 568/804; 568/790; 568/785
(58) Field of Search ................................ 568/804, 790, 568/785

(56) References Cited

U.S. PATENT DOCUMENTS

| 4,418,224 A | 11/1983 | Bennett et al. |
| 5,523,420 A | 6/1996 | Lowack et al. |

FOREIGN PATENT DOCUMENTS

| EP | 0419045 A1 | 3/1991 |
| EP | 1041061 A2 | 10/2000 |
| JP | 52111524 | 9/1977 |
| JP | 6025041 | 2/1994 |
| JP | 6116189 | 4/1994 |
| JP | 11228473 | 8/1999 |
| JP | 2000038363 | 2/2000 |
| WO | WO9815509 | 4/1998 |

Primary Examiner—J. Parsa
(74) Attorney, Agent, or Firm—Birch, Stewart, Kolasch & Birch, LLP

(57) ABSTRACT

A process for producing an aromatic ring alkylated phenols, wherein said process comprises reacting phenols represented by the general formula (1):

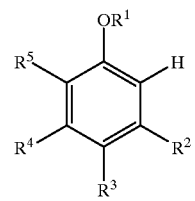

(1)

wherein, each of $R^1$, $R^2$, $R^3$, $R^4$ and $R^5$ independently represents a hydrogen atom, or a linear or branched alkyl group having 1 to 10 carbon atoms;

with monohydric or dihydric alcohol in the presence of a hydroxide of a metal, an alkoxide of a metal, or a hydroxide of a metal and an alkoxide of a metal under a supercritical state of the alcohol.

10 Claims, No Drawings

PROCESS FOR PRODUCING AROMATIC RING ALKYLATED PHENOLS

BACKGROUND OF THE INVENTION

1. Field of the Invention

The present invention relates to a process for producing an aromatic ring alkylated phenols.

2. Description of the Related Art

Aromatic ring alkylated phenols are industrially used as raw materials and intermediates of medical and agricultural medicines, resins, various additives, polymerization inhibitors, antioxidants, disinfectants, preservatives, industrial chemicals and the like. Among them, thymol having a structure in which an isopropyl group is bonded to 2-position and a methyl group is bonded to 5-position of phenol is in much demand as a vermicide. Further, 2,3,6-trimethylphenol is in much demand as a synthesis intermediate of trimethylhydroquinone which is a raw material of vitamin E. In an example for producing vitamin E from 2,3,6-trimethylphenol, in the first step, 2,3,6-trimethylphenol is oxidized to synthesis 2,3,6-trimethylbenzoquinone, and which is reduced to synthesize trimethylhydroquinone. In the second step, trimethylhydroquinone and phytol are reacted in the presence of an acid catalyst to synthesize vitamin E, according to U.S. Pat. No. 5,523,420.

Conventionally, for obtaining ortho-alkyled phenols, a gas phase reaction in which phenols and alcohol are vaporized, an passed through catalyst phase to cause a reaction thereof, a liquid phase reaction utilizing Friedel Craft's reaction, and the like, are known. For example, JP-A No. 6-25041 discloses a method in which phenols and alcohol are reacted in gas phase using manganese oxide as a catalyst to produce an aromatic ring alkylated derivative of phenols. However, this method has a problem that a reaction apparatus becomes complicated and bulky.

JP-A No. 2000-38363discloses a method in which phenols and alcohol are heated at 400° C. in a supercritical region using zirconium oxide as a catalyst, for alkylation. However, in this method, a large amount of catalyst is necessary, causing problems in cost and size of an apparatus.

SUMMARY OF THE INVENTION

The above-mentioned known method have a problem that a large and complicated reaction apparatus is necessary and a problem that a large amount of catalyst is required.

An object of the present invention is to provide a process for producing an aromatic ring alkylated phenols by using phenols and alcohol in a relatively smaller reaction vessel with a small amount of catalyst, at high reactivity.

Under these circumstances, the present inventors have intensively studied a process for producing an aromatic ring alkylated phenols from phenols, and found that an aromatic ring alkylated phenols can be easily obtained by reacting phenols with alcohols under a supercritical state in the presence of a hydroxide or alkoxide of a metal as a catalyst, and have completed the present invention.

Namely, the present invention relates to a process for producing an aromatic ring alkylated phenols, wherein said process comprises reacting phenols represented by the general formula (1):

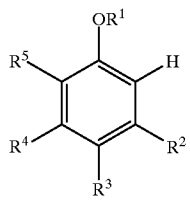

(1)

wherein, each of $R^1$, $R^2$, $R^3$, $R^4$ and $R^5$ independently represents a hydrogen atom, or a linear or branched alkyl group having 1 to 10 carbon atoms;

with monohydric or dihydric alcohol in the presence of a hydroxide of a metal, an alkoxide of a metal, or a hydroxide of a metal and an alkoxide of a metal under a supercritical state of the alcohol. [hereinafter, referred to as production method (I) of the present invention]

Further, the present invention relates to a process for producing an aromatic ring alkylated phenols, wherein said process comprises reacting phenols represented by the general formula (1) with monohydric or dihydric alcohol in the presence of carbon dioxide and, a hydroxide of a metal, an alkoxide of a metal or a hydroxide of a metal and an alkoxide of a metal under a supercritical state of the mixture of alcohol and carbon dioxide. [hereinafter, referred to as production method (II) of the present invention]

DETAILED DESCRIPTION OF THE PREFERRED EMBODIMENTS

The present invention will be illustrated in detail below.

As the linear or branched alkyl group having 1 to 10 carbon atoms represented by $R^1$, $R^2$, $R^3$, $R^4$ or $R^5$ in phenols represented by the general formula (1), used as a raw material in the present invention, a methyl group, ethyl group, n-propyl group, isopropyl group, n-butyl group, isobutyl group, t-butyl group and the like are listed, and specific examples of the phenols of the general formula (1) include phenol, o-cresol, m-cresol, p-cresol, 2,3-xylenol, 2,4-xylenol, 2,5-xylenol, 3,4-xylenol, 3,5-xylenol, anisole, t-butylphenol and the like.

Alcohol which is another starting material in the present invention is not particularly restricted providing it is monohydric or dihydric alcohol, and preferably monohydric alcohol represented by the general formula (2):

$$R^6—OH \qquad (2)$$

wherein, $R^6$ represent a linear or branched alkyl group having 1 to 10 carbon atoms. Here, as $R^6$, there are listed a methyl group, ethyl group, n-propyl group, isopropyl group, n-butyl group, isobutyl group, t-butyl group and the like.

As the monohydric alcohol represented by the general formula (2), methanol, ethanol, n-propanol, isopropanol, n-butanol, isobutanol, t-butanol, pentanol, hexanol, heptanol, n-octanol, n-nonanol, n-decanol and the like are listed, and methanol, ethanol, n-propanol and n-butanol are preferable, methanol and ethanol are more preferable, and methanol is further preferable.

As the dihydric alcohol, ethylene glycol, propylene glycol and the like are listed.

In the present invention, the molar ratio of monohydric or dihydric alcohol to phenols of the general formula (1) is appropriately determined depending on compound used, and usually from 1 to 1000, and preferably from 1 to 200.

In the production method (I) of the present invention, a reaction is conducted under a condition wherein monohydric or dihydric alcohol manifests supercritical state. In the production method (II) of the present invention, a reaction is conducted under a condition wherein a mixture of monohydric or dihydric alcohol and carbon dioxide manifests supercritical state.

Here, the supercritical condition means the following condition.

A substance manifests inherent three conditions of gas, liquid and solid, and when over the critical temperature and the critical pressure, fluid phase is formed which is not condensed even if pressure is applied. This condition is referred to as supercritical condition.

Fluid under supercritical condition shows different nature from usual natures of liquid and gas. Fluid under supercritical condition is a "solvent which is not liquid", in which the density thereof is near that of liquid, and the viscosity thereof is near that of gas, and heat conductivity and diffusion coefficient show intermediate natures between gas and liquid, and mass transfer becomes advantageous due to lower viscosity and higher diffusion property, and higher heat transferring property can be obtained because of higher conductivity.

When supercritical fluid is used as a reaction site, higher reactivity is obtained than usual gas phase and liquid phase since the reaction site is under conditions of higher density and higher diffusion property as described above.

Further, because supercritical condition has density near liquid phase, the size of a reaction apparatus thereof can be reduced as compared with gas phase.

In the present invention, the upper limit of reaction temperature is not restrictive, and preferably 450° C. or less so that phenols represented by the general formula (1) are not decomposed. The upper limit of reaction pressure is also no restrictive, and preferably 25 MPa or less since increase of pressure resistance of a reaction apparatus is expensive.

In the production method (I) of the present invention, it is necessary that a reaction is conducted under a condition wherein monohydric or dihydric alcohol manifests supercritical state. When methanol is used as the alcohol, a reaction is conducted under conditions of 240° C. or more and 8 MPa or more since methanol has a critical temperature of 240° C. and a critical pressure of 8 MPa. When ethanol is used, a reaction is conducted under conditions of 243° C. or more and 6.3 MPa or more since ethanol has a critical temperature of 243° C. and a critical pressure of 6.3 MPa. When n-propanol is used, a reaction is conducted under conditions of 264° C. or more and 5 MPa or more since n-propanol has a critical temperature of 264° C. and a critical pressure of 5 MPa. When isopropanol is used, a reaction is conducted under conditions of 235° C. or more and 4.8 MPa or more since isopropanol has a critical temperature of 235° C. and a critical pressure of 4.8 MPa. When n-butanol is used, a reaction is conducted under conditions of 287° C. or more and 4.8 MPa or more since n-butanol has a critical temperature of 287° C. and a critical pressure of 4.8 MPa.

Next, the production method (II) of the present invention will be illustrated.

In the production method (II) of the present invention, it is necessary that a reaction is conducted under a condition wherein a mixture of monohydric or dihydric alcohol and carbon dioxide manifests supercritical state, in the presence of a catalyst and carbon dioxide.

The mixing ratio of the above-mentioned alcohol and carbon dioxide is not particularly restricted, and is determined in view of solubility of phenols used in the reaction in the alcohol. The mixing ratio of the above-mentioned alcohol and carbon dioxide is preferably 10:90 to 99:1.

Cases in which methanol is used as the alcohol and phenol is used as the phenols will be illustrated specifically. For example, when the molar ratio of methanol to carbon dioxide is 75:25, this mixture has a critical temperature of 204° C. and a critical pressure of 12.75 MPa according to a literature, Journal of Chemical Thermodynamics, vol. 23, p. 970 (1991).

When an aromatic ring of phenols is methylated under temperature and pressure conditions wherein a mixture of methanol and carbon dioxide manifests supercritical condition, temperature and pressure conditions are necessary wherein the mixture manifests supercritical condition. For example, in the case of the above-mentioned mixture in which the molar ratio of methanol to carbon dioxide is 75:25, a temperature of 204° C. or more and a pressure of 12.75 MPa or more are necessary, and a temperature of 240° C. or more and a pressure of 12.75 MPa or more are more preferable.

The reaction time in the production method (I) of the present invention or the production method (II) of the present invention is appropriately determined, respectively, depending on kinds of the phenols and the alcohol, and usually in a range from 1 minute to 24 hours.

In the respective production method, the reaction has to be conducted in the presence of a catalyst, namely, a hydroxide of a metal, an alkoxide of a metal, a hydroxide of a metal and an alkoxide of a metal, and reactivity of alkylation of aromatic ring can be enhanced only by addition of a relatively small amount of the catalyst.

Typical examples of the hydroxide of a metal include, but are not limited to, lithium hydroxide, sodium hydroxide, potassium hydroxide, magnesium hydroxide, calcium hydroxide, barium hydroxide, strontium hydroxide, germanium hydroxide and the like.

The hydroxide may be combined with an alkoxide of a metal.

Examples of the alkoxide of a metal include, but are not limited to, lithium methylate, sodium methylate, potassium methylate, dimethoxymagnesium, dimethoxycalcium, dimethoxybarium, dimethoxystrontium, tetramethoxygermanium and the like.

The alkoxide may be combined with a hydroxide of a metal.

The present invention can be effected in various reaction embodiments. For example, it may be conducted by a batch system, or by a flow system, and the batch system is preferable.

An aromatic ring alkylated phenols represented by the general formula (1) is separated from reaction mixtures after completion of respective reaction of the production method (I) or the production method (II) at a purity necessary for various use. The reaction mixture may sometimes contains unreacted raw materials or other impurities in addition to the aromatic ring alkylated phenols.

The separation method is not particularly restricted, and general methods such as distillation, extraction and the like can be applied according to nature of the substituted compound.

Namely, according to the present invention, a method can be provided in which phenols represented by the general formula (1) and monohydric or dihydric alcohol are used, and an aromatic ring of the phenols is alkylated in a relatively smaller reaction vessel at higher reactivity, particularly by a batch system, with a small amount of a catalyst.

In the present invention, the addition amount of a catalyst is preferably from 0.01 to 20% by weight, more preferably from 0.05 to 2% by weight based on the phenols of the general formula (1) used in the reaction.

According to the present invention, an aromatic ring alkylated phenols can be easily obtained by reacting phenols with alcohols in a relatively smaller reaction vessel with a small amount of catalyst at high reactivity.

EXAMPLE

The following examples further illustrate the present invention in detail below, but do not limit the scope of the present invention.

Reaction materials and reaction products in examples were identified by using a gas chromatography mass analysis apparatus HP-6890 (GC: manufacture by Yokogawa Electric Corp.)-HP5973 (MS: manufacture by Yokogawa Electric Corp.) and analyzed quantitatively by using a gas chromatography apparatus GC-353B (manufactured by GL Science) equipped with FID (flame ionization detector). The conversion and selectivity in examples were calculated according to the following methods.

Conversion was calculated by the following formula:

(conversion)={1−(area of chromatograph of unreacted reaction substrates remaining in reaction solution)/(sum of areas of remaining reaction substrates and whole reaction product)}× 100%.

The selectivity was calculated by the following formula:

(selectivity)={(area of gas chromatograph of reaction product to be calculated)/(sum of areas of gas chromatograph of whole reaction product)}×100%, while hypothesizing that areas of gas chromatograph per mol of reaction products are equivalent.

Example 1

0.035 g of m-cresol (manufactured by Wako Pure Chemical Industries Ltd.), 1.358 g of methanol (manufactured by Wako Pure Chemical Industries Ltd.) and 0.33 mg of lithium hydroxide monohydrate (manufactured by Wako Pure Chemical Industries Ltd.) (0.94% by weight based on m-cresol) were charged in an autoclave (made of SUS316, inner volume: 4.5 ml) and heated up to 370° C. by a sand bath, to initiate a reaction. After 15 minutes, the autoclave was quenched, and the reaction solution was removed after the temperature of the autoclave reached room temperature. Quantification was conducted according to the above-mentioned method, as a result, the conversion of m-cresol was 64 mol %, the selectivity of 2,5-xylenol was 51 mol % and the selectivity of 2,3,6-trimethylphenol was 11 mol %. Regarding other components than these reaction products, the selectivity of 2,3-xylenol was 17 mol %, the selectivity of 3,4-xylenol was 5 mol %, the selectivity of m-methylanisole was 1 mol %, the sum of the selectivity of trimethylphenols other than 2,3,6-trimethylphenol was 4 mol %, and the selectivity of 2,3,4,6-tetramethylphenol was 1 mol %. The components were separated from the reaction solution by using liquid chromatography, and 2,5-xylenol and 2,3,6-trimethylphenyl were separated therefrom. The separated solutions were analyzed by using a gas chromatography mass analysis apparatus, to confirm that 2,5-xylenol and 2,3,6-trimethylphenol were separated from the product. Since the autoclave does not have a pressure gauge, the following experiment was conducted to estimate pressure during the reaction. Namely, a pressure gauge was installed to the same autoclave, the same amounts of m-cresol and methanol were charged and heated up to 370° C. by a sand bath, and the pressure was measured. The estimated value of the pressure during the reaction was 10 MPa.

Example 2

0.051 g of phenol (manufactured by Wako Pure Chemical Industries Ltd.), 1.358 g of methanol and 0.75 mg of lithium hydroxide monohydrate (0.15% by weight based on phenol) were charged in an autoclave (made of SUS316, inner volume: 4.5 ml, no pressure gauge) and heated up to 400° C. by a sand bath, to initiate a reaction. After 30 minutes, the autoclave was quenched, and the reaction solution was removed after the temperature of the autoclave reached room temperature. Quantification was conducted according to the above-mentioned method, as a result, the conversion of phenol was 36 mol %, the selectivity of o-cresol was 51 mol %, the selectivity of p-cresol was 10 mol %, the selectivity of 2,6-xylenol was 3 mol %, and the selectivity of 2,4-xylenol was 2 mol %. The components were separated from the reaction solution by using liquid chromatography, and o-cresol, p-cresol, 2,6-xylenol and 2,4-xylenol were separated therefrom. The separated solutions were analyzed by using a gas chromatography mass analysis apparatus, to confirm that o-cresol, p-cresol, 2,6-xylenol and 2,4-xylenol were separated from the product. Since the autoclave does not have a pressure gauge, the following experiment was conducted to estimate pressure during the reaction. Namely, a pressure gauge was installed to the same autoclave, the same amounts of phenol and methanol were charged and heated up to 400° C. by a sand bath, and the pressure was measured. The estimated value of the pressure during the reaction was 14.7 MPa.

Comparative Example 1

0.051 g of phenol, 1.352 g of methanol and 1.0 mg of zirconium oxide (manufactured by Kojundo Kagaku K.K.) (2.0% by weight based on phenol) were charged in an autoclave (made of SUS316, inner volume: 4.5 ml, no pressure gauge) and heated up to 400° C. by a sand bath, to initiate a reaction. After 30 minutes, the autoclave was quenched, and the reaction solution was removed after the temperature of the autoclave reached room temperature. Quantification was conducted according to the above-mentioned method, as a result, the conversion of phenol was 20 mol %, the selectivity of o-cresol was 50 mol %, the selectivity of p-cresol was 3 mol %, the selectivity of 2,6-xylenol was 2 mol %, and the selectivity of 2,4-xylenol was 1 mol %. Since the autoclave does not have a pressure gauge, the following experiment was conducted to estimate pressure during the reaction. Namely, a pressure gauge was installed to the same autoclave, the same amounts of phenol and methanol were charged and heated up to 400° C. by a sand bath, and the pressure was measured. The estimated value of the pressure during the reaction was 14.7 MPa.

Comparative Example 2

0.052 g of phenol, 1.358 g of methanol and 1.1 mg of zinc oxide (manufactured by Wako Pure Chemical Industries Ltd.)(2.1% by weight based on phenol) were charged in an autoclave (made of SUS316, inner volume: 4.5 ml, no pressure gauge) and heated up to 400° C. by a sand bath, to initiate a reaction. After 30 minutes, the autoclave was quenched, and the reaction solution was removed after the temperature of the autoclave reached room temperature. Quantification was conducted according to the above-mentioned method, as a result, the conversion of phenol was 11 mol %, the selectivity of o-cresol was 78 mol %, the selectivity of p-cresol was 2 mol %, the selectivity of 2,6-xylenol was 3 mol %, and 2,4-xylenol was not produced. Since the autoclave does not have a pressure gauge, the following experiment was conducted to estimate pressure during the reaction. Namely, a pressure gauge was installed to the same autoclave, the same amounts of phenol and methanol were charged and heated up to 400° C. by a sand bath, and the pressure was measured. The estimated value of the pressure during the reaction was 14.7 MPa.

Example 3

0.045 g of p-cresol (manufactured by Wako Pure Chemical Industries Ltd.), 1.485 g of methanol and 0.25 mg of lithium hydroxide monohydrate (0.56% by weight based on p-cresol) were charged in an autoclave (made of SUS316, inner volume: 4.5 ml, no pressure gauge) and heated up to 400° C. by a sand bath, to initiate a reaction. After 30 minutes, the autoclave was quenched, and the reaction solution was removed after the temperature of the autoclave reached room temperature. Quantification was conducted according to the above-mentioned method, as a result, the conversion of p-cresol was 97 mol %, and the selectivity of 2,4-xylenol was 23 mol %, and the selectivity of 2,4,6-trimethylphenol was 61 mol %. The components were separated from the reaction solution by using liquid chromatography, and 2,4-xylenol and 2,4,6-trimethylphenol were separated therefrom. The separated solutions were analyzed by using a gas chromatography mass analysis apparatus, to confirm that 2,4-xylenol and 2,4,6-trimethylphenol were separated from the product. Since the autoclave does not have a pressure gauge, the following experiment was conducted to estimate pressure during the reaction. Namely, a pressure gauge was installed to the same autoclave, the same amounts of p-cresol and methanol were charged and heated up to 400° C. by a sand bath, and the pressure was measured. The estimated value of the pressure during the reaction was 15.4 MPa.

Comparative Example 3

0.051 g of p-cresol, 1.350 g of methanol and 1.2 mg of zirconium oxide (2.4% by weight based on p-cresol) were charged in an autoclave (made of SUS316, inner volume: 4.5 ml, no pressure gauge) and heated up to 400° C. by a sand bath, to initiate a reaction. After 30 minutes, the autoclave was quenched, and the reaction solution was removed after the temperature of the autoclave reached room temperature. Quantification was conducted according to the above-mentioned method, as a result, the conversion of p-cresol was 8 mol %, the selectivity of 2,4-xylenol was 30 mol %, and 2,4,6-trimethylphenol was not produced. Since the autoclave does not have a pressure gauge, the following experiment was conducted to estimate pressure during the reaction. Namely, a pressure gauge was installed to the same autoclave, the same amounts of p-cresol and methanol were charged and heated up to 400° C. by a sand bath, and the pressure was measured. The estimated value of the pressure during the reaction was 14.7 MPa.

Comparative Example 4

0.052 g of p-cresol, 1.355 g of methanol and 1.3 mg of zinc oxide (2.3% by weight based on p-cresol) were charged in an autoclave (made of SUS316, inner volume: 4.5 ml, no pressure gauge) and heated up to 400° C. by a sand bath, to initiate a reaction. After 30 minutes, the autoclave was quenched, and the reaction solution was removed after the temperature of the autoclave reached room temperature. Quantification was conducted according to the above-mentioned method, as a result, the conversion of p-cresol was 12 mol %, the selectivity of 2,4-xylenol was 81 mol % and the selectivity of 2,4,6-trimethylphenol was 4 mol %. Since the autoclave does not have a pressure gauge, the following experiment was conducted to estimate pressure during the reaction. Namely, a pressure gauge was installed to the same autoclave, the same amounts of p-cresol and methanol were charged and heated up to 400° C. by a sand bath, and the pressure was measured. The estimated value of the pressure during the reaction was 14.7 MPa.

Example 4

0.412 g of m-cresol, 1.500 g of isopropanol and 1.9 mg of lithium hydroxide (0.46% by weight based on m-cresol) were charged in an autoclave (made of SUS316, inner volume: 4.5 ml, no pressure gauge) and heated up to 400° C. by a sand bath, to initiate a reaction. After 30 minutes, the autoclave was quenched, and the reaction solution was removed after the temperature of the autoclave reached room temperature. Quantification was conducted according to the above-mentioned method, as a result, the conversion of m-cresol was 22 mol %, and the selectivity of thymol was 62 mol %. Since the autoclave does not have a pressure gauge, the following experiment was conducted to estimate pressure during the reaction. Namely, a pressure gauge was installed to the same autoclave, the same amounts of m-cresol and isopropanol were charged and heated up to 400° C. by a sand bath, and the pressure was measured. The estimated value of the pressure during the reaction was 10 MPa.

What is claimed is:

1. A process for producing an aromatic ring alkylated phenols, wherein said process comprises reacting phenols represented by the general formula (1):

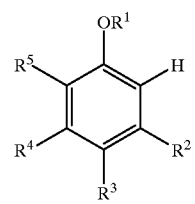

(1)

wherein, each of $R^1$, $R^2$, $R^3$, $R^4$ and $R^5$ independently represents a hydrogen atom, or a linear or branched alkyl group having 1 to 10 carbon atoms;

with monohydric or dihydric alcohol in the presence of a hydroxide of a metal, an alkoxide of a metal, or a hydroxide of a metal and an alkoxide of a metal under a supercritical state of the alcohol.

2. The process according to claim 1, wherein said process comprises reacting phenols represented by the general formula (1) with monohydric or dihydric alcohol in the presence of carbon dioxide and, a hydroxide of a metal, an alkoxide of a metal or a hydroxide of a metal and an alkoxide of a metal under a supercritical state of the mixture of alcohol and carbon dioxide.

3. The process according to claim 1, wherein the monohydric alcohol is alcohol represented by the general formula (2):

$$R^6 \text{—OH} \tag{2}$$

wherein, $R^6$ represent a linear or branched alkyl group having 1 to 10 carbon atoms.

4. The process according to claim 2, wherein the monohydric alcohol is alcohol represented by the general formula (2):

$$R^6 \text{—OH} \tag{2}$$

wherein, $R^6$ represent a linear or branched alkyl group having 1 to 10 carbon atoms.

5. The process according to claim 3, wherein $R^6$ in the general formula (2) is a methyl group.

6. The process according to claim 4, wherein $R^6$ in the general formula (2) is a methyl group.

7. The process according to claim 1, wherein the hydroxide of a metal is lithium hydroxide, sodium hydroxide, potassium hydroxide or calcium hydroxide.

8. The process according to claim 2, wherein the hydroxide of a metal is lithium hydroxide, sodium hydroxide, potassium hydroxide or calcium hydroxide.

9. The process according to claim 1, wherein the alkoxide of a metal is lithium methylate, sodium methylate or potassium methylate.

10. The process according to claim 2, wherein the alkoxide of a metal is lithium methylate, sodium methylate or potassium methylate.

* * * * *